US00PP21123P2

(12) United States Plant Patent
Perkins

(10) Patent No.: US PP21,123 P2
(45) Date of Patent: Jun. 29, 2010

(54) ***ANGELONIA* PLANT NAMED 'CAS LAVENER'**

(50) Latin Name: *Angelonia angustifolia*
Varietal Denomination: Cas Lavener

(75) Inventor: Ralph T. Perkins, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,364

(22) Filed: Nov. 7, 2008

(51) Int. Cl.
*A01H 5/00* (2006.01)

(52) U.S. Cl. ..... Plt./404

(58) Field of Classification Search ..... Plt./404
See application file for complete search history.

*Primary Examiner*—Annette H Para
*Assistant Examiner*—Louanne C Krawczewicz Myers
(74) *Attorney, Agent, or Firm*—S. Matthew Edwards

(57) ABSTRACT

A new *Angelonia* plant named 'Cas Lavener', articularly distinguished by the purple-violet flower color, slightly upright and semi-trailing habit with dense foliage and branching, exceptional heat tolerance, and good vigor.

1 Drawing Sheet

Latin name of genus and species of the plant claimed: *Angelonia angustifolia.*

Varietal denomination: 'Cas Lavener'.

BACKGROUND OF THE NEW PLANT

The present invention comprises a new *Angelonia*, botanically known as *Angelonia angustifolia*, and hereinafter referred to by the variety name 'Cas Lavener'.

'Cas Lavener' is a product of a planned breeding program. The new cultivar 'Cas Lavener' has a purple-violet flower color, slightly upright and semi-trailing habit with dense foliage and branching, exceptional heat tolerance, and good vigor.

'Cas Lavener' originated from a hybridization in a controlled breeding program in Gilroy, Calif. USA. The female parent was an unpatented hybrid seedling identified as '432-1' with a lavender and white color. '432-1' has fewer branches and darker and larger foliage than 'Cas Lavener'.

The male parent of 'Cas Lavener' was an unpatented hybrid seedling identified as '421-3' with a deep lavender color. '421-3' has smaller flowers, fewer branches, and is more prostrate than 'Cas Lavener'.

'Cas Lavener' was selected as one flowering plant within the progeny of the stated cross in 2006 in a controlled environment in Gilroy, Calif. USA. The pollination took place in September 2003 and the seed sowing in March 2006 all in a controlled environment in Gilroy, Calif., USA.

The first act of asexual reproduction of 'Cas Lavener' was accomplished using vegetative cuttings from the initial selection in June 2006 in a controlled environment in Gilroy, Calif. USA.

Horticultural examination of plants grown from cuttings of the plant initiated in June 2006 in Gilroy, Calif. USA, and continuing thereafter, has demonstrated that the combination of characteristics as herein disclosed for 'Cas Lavener' are firmly fixed and are retained through successive generations of asexual reproduction.

'Cas Lavener' has not been observed under all possible environmental conditions. The phenotype may vary significantly with variations in environment such as temperature, light intensity and day length.

A Plant Breeder's Right for this cultivar was applied for in Canada on Dec. 24, 2007 (PBR 07-6080). 'Cas Lavener' has not been made publicly available more than one year prior to the filing of this application.

DESCRIPTION OF THE DRAWINGS

The accompanying photographic drawing shows typical flower and foliage characteristics of 'Cas Lavener' with colors being as true as possible with an illustration of this type. The photographic drawing shows a container consisting of 3 flowering potted plants of the new variety and a close-up of the flower. Both photographs were taken in the spring of 2008 in Gilroy, Calif., USA. Both were grown in Gilroy, Calif., USA and were approximately 3–4 months old.

DETAILED BOTANICAL DESCRIPTION

The measurements were taken in Gilroy, Calif. USA, in April 2008 on plants that were growing in gallon pots in a greenhouse. Culture of these plants started about January 2008. These plants are about 3 months old.

Color Chart used: Royal Horticultural Society Colour Chart (R.H.S.) 2001.

BRIEF SUMMARY OF INVENTION

The following observations, measurements, and comparisons describe plants grown outside in Gilroy, Calif. USA. The following traits have been repeatedly observed and are determined to be basic characteristics of the new variety. The combination of these characteristics distinguishes this *Angelonia* as a new and distinct variety.

TABLE 1

DIFFERENCES BETWEEN THE NEW VARIETY 'CAS LAVENER' AND A SIMILAR VARIETY

| | 'Cas Lavener' | 'Balangbeke' (U.S. Plant Pat. No. 15,546) |
|---|---|---|
| Branching habit | More branch/fuller habit | Less branching/less dense habit |
| Foliage color | Darker green | Lighter green |
| Flower color | Slightly darker (N82A) | Slightly lighter (N87B |

Plant:

*Form, growth and habit.*—Slightly upright and semi-trailing, dense foliage, good branching.

*Plant height.*—8—10 cm.

*Plant height* (*inflorescence included*).—10–12 cm.

*Plant width.*—30–45 cm.

FOLIAGE

*Immature, leaf color, upper surface.*—Closest to RHS 137B.

*Lower surface.*—Closest to RHS 137B.

*Mature, leaf color, upper surface.*—Closest to RHS 137A.

*Lower surface.*—Closest to RHS 137B.

*Length.*—6.3–8.0 cm.

*Width.*—1.2–1.3 cm.

*Shape.*—Narrowly elliptical.

*Base shape.*—Cuncate.

*Apex shape.*—Acute.

*Margin.*—Serrate to serrulate.

*Texture, upper surface.*—Smooth.

*Texture, lower surface.*—Few glandular hairs on margins.

*Color of veins, upper and lower surfaces.*—RHS 145B.

*Vein pattern.*—Pinnate.

Stem:

*Number of main stems per plant.*—6–8.

*Number of leaves per stem* (*before it branches*).—20–26.

*Color of stem.*—RHS 144B.

*Length of stem.*—17–20 cm.

*Diameter.*—0.2 cm.

*Length of internodes.*—1.5–3.0 cm.

*Texture.*—Glandular hairs.

Inflorescence:

*Type.*—Terminal raceme; florets, solitary in leaf axis but sometimes have 2.

*Number of flowers per raceme.*—16–22.

*Raceme length.*—11–19 cm.

*Raceme diameter.*—0.2 cm.

*Color of pedicel.*—RHS 176A.

*Length of pedicel.*—1.5–1.7 cm.

*Diameter of pedicel.*—0.5 cm.

*Texture.*—Glandular hairs.

Corolla:

*Form.*—Single, two-lipped (5 petaled, fused at base)

*Length of floret.*—2.2–2.3 cm.

*Width of floret.*—2.1–2.3 cm.

*Flower tube length.*—1.5 cm.

*Throat diameter.*—1.0 cm.

*Color upper lip petals, upper surface.*—RHS N82A but a little darker maturing to RHS N82A.

*Color upper lip petals, lower surface.*—RHS N82A.

*Size upper lip petal length.*—0.7–0.8 cm from corolla opening.

*Size upper lip petal width.*—0.9–1.1 cm.

*Color lower lip, lateral petals, upper surface.*—RHS 82A maturing to RHS N82B, slight spotting of RHS N79B to C.

*Color lower lip, lateral petals, lower surface.*—RHS N82A.

*Size lower lip, lateral petals length.*—0.8–0.9 cm from corolla opening.

*Size lower lip, lateral petals width.*—1.0–1.1 cm.

*Color lower lip, mid-petal, upper surface.*—RHS N82A maturing to RHS N82B, slight spotting of RHS N79B to C, over a base of RHS N155D but whiter.

*Color lower lip, mid-petal, lower surface.*—RHS N82A maturing to RHS N82B with slight blotching of RHS N79B to C; RHS 155C large basal blotch with slight spots of RHS N79C; and RHS 144B at the corolla ridge.

*Size lower lip, mid-petal length.*—1.2–1.3 cm from corolla opening.

*Size lower lip, mid-petal width.*—0.9–1.1 cm.

Petal shape.—Obovate.

*Apex shape.*—Rounded.

*Margin.*—Entire.

*Petal texture, upper surface.*—Papillose, glandular hairs.

*Petal texture, lower surface.*—Papillose.

*Corolla color, inside.*—RHS N155B; RHS N79B blotches.

*Corolla color, outside.*—RHS N155B; RHS N79B blotches though more subdued than the inside.

*Corolla texture, inside surface.*—Glandular hairs.

*Corolla texture, outside surface.*—Smooth.

*Duration of flowering.*—Continuous flowering throughout the Summer.

*Fragrance.*—None.

*Lastingness of individual florets.*—About 6–7 days.

Bud (just before opening):

*Color.*—RHS 145C with a bit of RHS 79D but a little greyer than what would be on the dorsal lip petal.

*Length.*—0.7–0.8 cm.

*Width.*—0.6–0.7 cm.

*Shape.*—Obicular.

*Number of sepals.*—5 fused at base.

*Color of sepals, upper/inner surface.*—RHS 147A.

*Color of sepals, outer surface.*—RHS 147A but darker.

*Length of sepals.*—0.3–0.4 cm.

*Width of sepals.*—0.15 cm.

*Sepal shape.*—Ovate.

*Apex shape.*—Acute.

*Margins.*—Entire.

*Texture.*—Glandular hairs on both sides.

Reproductive organs:

*Pistil.*—1.

*Pistil length.*—0.5 cm.

*Style color.*—RHS 69D.

*Stigma color.*—Ringed in RHS N82C and RHS 96C.

*Ovaries.*—Not observed.

*Stamens.*—4, in pairs.

*Color of filaments.*—RHS 96D.

*Length of filaments.*—0.5 cm.

*Anther color.*—RHS 200A.

*Anther length.*—0.1 cm.

*Anther shape.*—Oblong.

*Pollen amount.*—Very sparse.

*Color of pollen.*—RHS 158B.

*Fertility/seed set.*—Not observed on this hybrid.

Disease/pest resistance: Disease resistance or susceptibility has not been observed on this hybrid.

What is claimed is:

1. A new and distinct variety of *Angelonia* plant named 'Cas Lavener', substantially as illustrated and described herein.

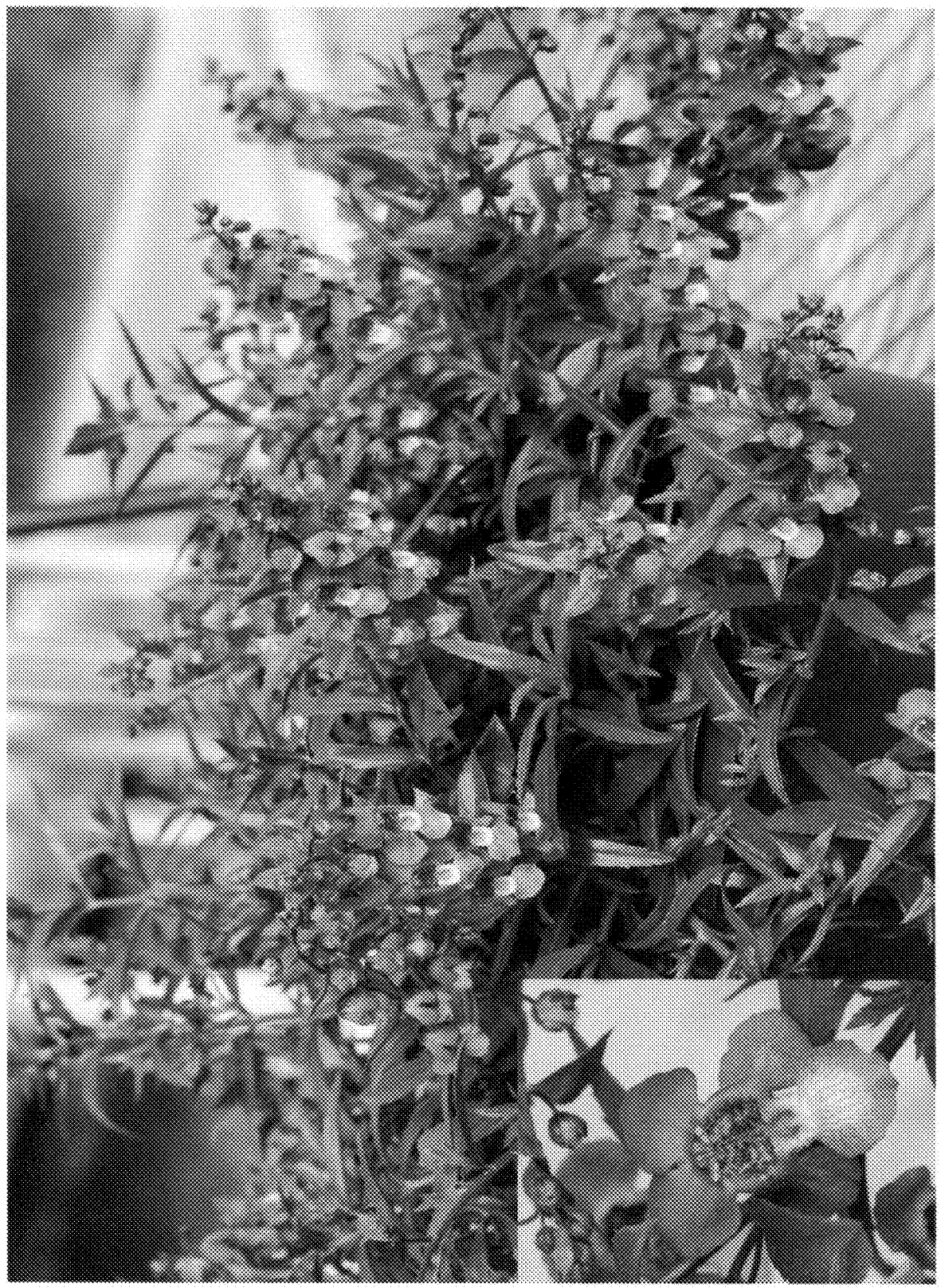

* * * * *